United States Patent
Rassatt et al.

(10) Patent No.: US 8,945,090 B2
(45) Date of Patent: Feb. 3, 2015

(54) IMPLANTABLE RADIOPAQUE MARKING

(75) Inventors: Bradley B. Rassatt, Apple Valley, MN (US); Joel T. Eggert, Champlin, MN (US); Cory P. Wright, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1076 days.

(21) Appl. No.: 12/953,031

(22) Filed: Nov. 23, 2010

(65) Prior Publication Data

US 2011/0160558 A1 Jun. 30, 2011

Related U.S. Application Data

(60) Provisional application No. 61/290,871, filed on Dec. 29, 2009.

(51) Int. Cl.
| | | |
|---|---|---|
| *A61M 25/098* | (2006.01) | |
| *A61N 1/05* | (2006.01) | |
| *A61B 19/00* | (2006.01) | |
| *A61B 5/04* | (2006.01) | |
| *A61N 1/08* | (2006.01) | |

(52) U.S. Cl.
CPC . *A61N 1/05* (2013.01); *A61B 19/44* (2013.01); *A61B 2019/446* (2013.01); *A61B 2019/5466* (2013.01); *A61N 2001/086* (2013.01)
USPC .............................. 604/529; 600/372; 600/508

(58) Field of Classification Search
CPC .................. A61B 2019/5466; A61M 25/0108; A61M 25/09; A61M 2025/1079; A61M 2025/1093; A61M 2025/09166; A61N 2001/086
USPC ......... 600/372–375, 377–378, 382, 385, 393, 600/508–509; 604/103.1, 523, 529, 532
See application file for complete search history.

(56) References Cited

U.S. PATENT DOCUMENTS

| | | | | |
|---|---|---|---|---|
| 5,253,653 | A | * | 10/1993 | Daigle et al. .................. 600/585 |
| 5,366,494 | A | * | 11/1994 | Holleman et al. ............ 607/119 |
| 6,210,396 | B1 | | 4/2001 | MacDonald et al. |
| 6,340,368 | B1 | | 1/2002 | Verbeck |
| 2008/0021313 | A1 | | 1/2008 | Eidenschink et al. |

FOREIGN PATENT DOCUMENTS

| | | |
|---|---|---|
| WO | WO-0232500 A1 | 4/2002 |
| WO | WO-2004103466 A1 | 12/2004 |
| WO | WO-2007081551 A1 | 7/2007 |

OTHER PUBLICATIONS

"Medtronic Begins First-Ever Study to Evaluate New Pacemaker System Designed for Safe Use with MRI Machines", Medtronic http://wwwp.medtronic.com/Newsroom/NewsReleaseDetails.do?itemid=1170952028478&format=pdf&lang=en_US, (Feb. 9, 2007), 3 pgs.

Burrows, Jeff, "Innehållet i denna fil får endast användas för privet bruk. Kopiering eller annan användning kräver tillstånd från", Medtronic Inc, (2008), 24 pgs.

* cited by examiner

*Primary Examiner* — Linda Dvorak
*Assistant Examiner* — Brian M Antiskay
(74) *Attorney, Agent, or Firm* — Schwegman Lundberg & Woessner, P.A.

(57) ABSTRACT

Specified information can be provided to a user, to a machine, or to an automated process using a specified configuration of a plurality of radiopaque rings about at least a portion of an implantable lead.

17 Claims, 3 Drawing Sheets

IMPLANTABLE RADIOPAQUE MARKING

CLAIM OF PRIORITY

This application claims the benefit of priority under 35 U.S.C. §119(e) to Rassatt et al. U.S. Provisional Patent Application Ser. No. 61/290,871, entitled "IMPLANTABLE RADIOPAQUE MARKING," filed on Dec. 29, 2009, which is hereby incorporated by reference herein in its entirety.

BACKGROUND

Implantable medical devices (IMDs) can perform a variety of diagnostic or therapeutic functions. For example, an IMD can include one or more cardiac function management features, such as to monitor or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), or cardiac resynchronization therapy (CRT) devices, among others. Nuclear magnetic resonance imaging (MRI) is a medical imaging technique that can be used to visualize internal structure of the body. MRI is an increasingly common diagnostic tool, but can pose risks to a person with an IMD, such as a patient undergoing an MRI scan or a person nearby MRI equipment, or to people having a conductive implant.

OVERVIEW

In an example, specified information can be provided to a user, to a machine, or to an automated process using a specified configuration of a plurality of radiopaque rings about at least a portion of an implantable lead.

In Example 1, a system includes an implantable lead including a plurality of radiopaque rings arranged in a specified configuration about a portion of the implantable lead, wherein the specified configuration of the plurality of radiopaque rings is configured to provide specified information to a user, to a machine, or to an automated process.

In Example 2, each of the plurality of radiopaque rings of Example 1 optionally have different inner diameters.

In Example 3, the implantable lead of any one or more of Examples 1-2 optionally includes a rear seal configured to be at least partially inserted into a lead port of an implantable medical device (IMD) header, wherein the plurality of radiopaque rings of any one or more of Examples 1-2 are optionally configured to be injection molded into the rear seal.

In Example 4, the specific configuration of the plurality of radiopaque rings of any one or more of Examples 1-3 optionally includes the number of radiopaque rings, wherein different numbers of radiopaque rings are configured to provide different information.

In Example 5, the specific configuration of the plurality of radiopaque rings of any one or more of Examples 1-4 optionally includes at least one of a radiopaque ring shape, a radiopaque ring inner or outer diameter, one or more spacings between radiopaque rings, or a combination of at least one of the radiopaque ring shape, the radiopaque ring inner or outer diameter, or the one or more spacings between radiopaque rings.

In Example 6, different specified configurations of any one or more of Examples 1-5 are optionally configured to provide different information to the user.

In Example 7, the specified configuration of the plurality of radiopaque rings of any one or more of Examples 1-6 is optionally configured to provide an indication of a level of magnetic resonance (MR) compatibility of the implantable lead.

In Example 8, a first specified configuration of any one or more of Examples 1-7 is optionally configured to optionally provide an indication that the implantable lead is MR Conditional to a first magnetic field strength, and a second specified configuration of any one or more of Examples 1-6 is optionally configured to provide an indication the implantable lead is MR Conditional to a second magnetic field strength, wherein the second specified configuration is optionally different than the first specified configuration and the second magnetic field strength is optionally different than the first magnetic field strength. In Example 9, the first specified configuration of any one or more of Examples 1-8 optionally includes a first number of radiopaque rings and the second specified configuration includes a second number of radiopaque rings, wherein the second number is optionally different than the first number.

In Example 10, a system includes an implantable lead including a rear seal configured to be at least partially inserted into a lead port of an implantable medical device (IMD) header and a plurality of radiopaque rings each having different inner diameters arranged in a specified configuration about a portion of the implantable lead, wherein the plurality of radiopaque rings are configured to be injection molded into the rear seal, and wherein the specified configuration of the plurality of radiopaque rings is configured to provide specified information to a user, to a machine, or to an automated process.

In Example 11, the specified configuration of the plurality of radiopaque rings of any one or more of Examples 1-10 is optionally configured to provide an indication of a level of magnetic resonance (MR) compatibility of the implantable lead, wherein a first specified configuration of any one or more of Examples 1-10 is optionally configured to provide an indication that the implantable lead is MR Conditional to a first magnetic field strength and a second specified configuration of any one or more of Examples 1-10 is optionally configured to provide an indication the implantable lead is MR Conditional to a second magnetic field strength, the second specified configuration optionally different than the first specified configuration and the second magnetic field strength optionally different than the first magnetic field strength, wherein the first specified configuration optionally includes a first number of radiopaque rings and the second specified configuration optionally includes a second number of radiopaque rings, wherein the second number is optionally different than the first number.

In Example 12, a method includes providing specified information to a user, to a machine, or to an automated process using a specified configuration of a plurality of radiopaque rings about at least a portion of an implantable lead.

In Example 13, each of the plurality of radiopaque rings of any one or more of Examples 1-12 optionally have different inner diameters.

In Example 14, the providing the specified information of any one or more of Examples 1-13 optionally includes using a specified configuration of a plurality of radiopaque rings injection molded into a rear seal, the rear seal configured to be at least partially inserted into an implantable medical device (IMD) header.

In Example 15, the providing the specified information using the specified configuration of any one or more of Examples 1-14 optionally includes using the number of radiopaque rings, and wherein different numbers of radiopaque rings are optionally configured to provide different information.

In Example 16, the providing the specified information using the specified configuration of any one or more of Examples 1-15 optionally includes using at least one of a radiopaque ring shape, a radiopaque ring inner or outer diameter, one or more spacings between radiopaque rings, or a combination of at least one of the radiopaque ring shape, the radiopaque ring inner or outer diameter, or the one or more spacings between radiopaque rings.

In Example 17, the providing the specified information of any one or more of Examples 1-16 optionally includes providing different information using different specified configurations.

In Example 18, the providing the specified information using the specified configuration of any one or more of Examples 1-17 optionally includes providing an indication of a level of magnetic resonance (MR) compatibility of the implantable lead.

In Example 19, the method of any one or more of Examples 1-18 optionally includes providing an indication that the implantable lead is MR Conditional to a first magnetic field strength using a first specified configuration, and providing an indication the implantable lead is MR Conditional to a second magnetic field strength using a second specified configuration, the second specified configuration optionally different than the first specified configuration and the second magnetic field strength optionally different than the first magnetic field strength.

In Example 20, the using the first specified configuration of any one or more of Examples 1-19 optionally includes using a first number of radiopaque rings and the using the second specified configuration of any one or more of Examples 1-19 optionally includes using a second number of radiopaque rings, the second number optionally different than the first number.

In Example 21, a system can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

The examples provided herein can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
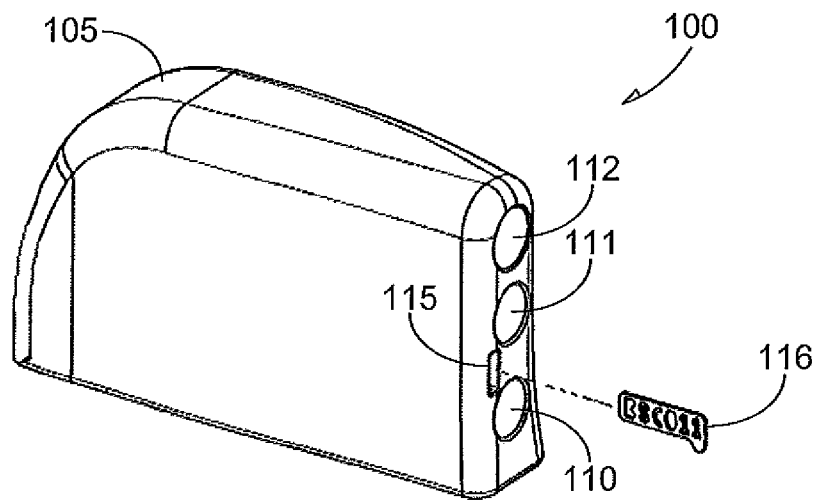
FIG. 1 illustrates generally an example of a system including an IMD header including a first lead port, a second lead port, a third lead port, and an identification (ID) cavity configured to receive a first radiopaque X-Ray identifier.

Nuclear magnetic resonance (NMR) devices (e.g., an MRI seamier, an NMR spectrometer, or other NMR device) can produce both static and time-varying magnetic fields. For example, an MRI scanner can provide a strong static magnetic field, $B_0$, such as to align nuclei within a subject to the axis of the $B_0$ field. The $B_0$ can provide a slight net magnetization (e.g., a "spin polarization") among the nuclei in bulk because the spin states of the nuclei are not randomly distributed among the possible spin states. Because the resolution attainable by NMR devices can be related to the magnitude of the $B_0$ field, a stronger $B_0$ field can be used to spin polarize the subject's nuclei to obtain finer resolution images. NMR devices can be classified according the magnitude of the $B_0$ field used during imaging, such as a 1.5 Tesla $B_0$ field, a 3.0 Tesla $B_0$ field, etc.

After nuclei are aligned using the $B_0$ field, one or more radio frequency (RF) magnetic excitation pulses can be delivered such as to alter the alignment of specified nuclei (e.g., within a particular volume or plane to be imaged within the subject). The power, phase, and range of frequencies of the one or more RF excitation pulses can be selected, such as depending on the magnitude of the $B_0$ field, the type or resonant frequency of the nuclei to be imaged, or one or more other factors. After the RF excitation pulses are turned off, one or more RF receivers can be used to detect a time-varying magnetic field (e.g., a flux) developed by the nuclei as they relax back to a lower energy state, such as the spin polarized state induced by the static magnetic field, $B_0$.

One or more gradient magnetic fields can also be provided during magnetic resonance (MR), such as to create a slight position-dependent variation in the static polarization field. The variation in the static polarization field slightly alters the resonant frequency of the relaxing nuclei, such as during relaxation after excitation by the one or more RF pulses. Using the gradient field along with the static field can provide "spatial localization" of signals detected by the RF receiver, such as by using frequency discrimination. Using a gradient field can allow a volume or a plane to be imaged more efficiently. In a gradient field example, signals received from relaxing nuclei can include energy in respective unique frequency ranges corresponding to the respective locations of the nuclei.

Active MRI equipment can induce unwanted torques, forces, or heating in an IMD or other conductive implant, or can interfere with operation of the IMD. In certain examples, the interference can include disruption in sensing by the IMD, interference in communication between the IMD and other implants or external modules during MRI operation, or disruption in monitoring or therapeutic function of the IMD.

During an MRI scan, the one or more RF excitation pulses can include energy delivered at frequencies from less than 10 MHz to more than 100 MHz, such as corresponding to the nuclear magnetic resonances of the subject nuclei to be imaged. The gradient magnetic field can include energy delivered at frequencies lower than the RF excitation pulses, because most of the AC energy included in the gradient field is provided when the gradient field is ramping or "slewing." The one or more gradient magnetic fields can be provided in multiple axes, such as including individual time-varying gradient fields provided in each of the axes to provide imaging in multiple dimensions.

In an example, the static field, $B_0$, can induce unwanted forces or torques on ferromagnetic materials, such as steel or nickel. The forces or torques can occur even when the materials are not directly within the "bore" of the MRI equipment, because significant fields can exist near the MRI equipment. Moreover, if an electric current is switched on or off in the presence of the $B_0$ field, a significant torque or force can be suddenly imposed in the plane of the circulation of the current, even though the $B_0$ field itself is static. The induced force or torque can be minimal for small currents, but the torque can be significant for larger currents, such as those delivered during shock therapy. For example, assuming the circulating current is circulating in a plane normal (e.g., perpendicular) to the static field, the torque can be proportional to the magnitude of the $B_0$ field, multiplied by the surface area of the current loop, multiplied by the current.

Time-varying fields, such as the gradient field or the field associated with the RF excitation pulse, can present different risks than the static field, $B_0$. For example, the behavior of a wire loop in the presence of a time-varying magnetic field can be described using Faraday's law, which can be represented by $$\varepsilon = -\frac{d\Phi_{B_1}}{dt},$$

in which $\varepsilon$ can represent the electromotive force (e.g., in volts), such as developed by a time-varying magnetic flux. The magnetic flux can be represented as $$\Phi_{B1} = \int\int_S B_1 \cdot dS,$$

in which $B_1$ can represent an instantaneous magnetic flux density vector (e.g., in Webers per square meter, or Tesla). If $B_1$ is relatively uniform over the surface S, then the magnetic flux can be approximately $\Phi_{B_1}=|B_1||A|$, where A can represent the area of the surface S. Operating MRI equipment can produce a time-varying gradient field having a slew rates in excess of 100 Tesla per second (T/s). The slew rate can be similar to a "slope" of the gradient field, and is thus similar to $$\frac{d\Phi_{B_1}}{dt}.$$

The electromotive force (EMF) of Faraday's law can cause an unwanted heating effect in a conductor, regardless of whether the conductor is ferromagnetic. EMF can induce current flow in a conductor (e.g., a housing of an IMD, one or more other conductive regions within an IMD, or one or more other conductive implants). The induced current can dissipate energy and can oppose the direction of the change of the externally applied field (e.g., given by Lenz's law). The induced current tends to curl away from its initial direction, forming an "eddy current" over the surface of the conductor, such as due to Lorentz forces acting upon electrons moving through the conductor. Because non-ideal conductors have a finite resistivity, the flow of induced current through the conductor can dissipate heat. The induced heat can cause a significant temperature rise in or near the conductor over the duration of the scan. The power dissipated by the eddy current can be proportional to the square of both the peak flux density and the frequency of the excitation.

Generally, induced currents, such as induced by the RF magnetic excitation pulse, can concentrate near the surface of a conductor, a phenomenon that can be referred to as the skin effect. The skin effect can limit both the magnitude and depth of the induced current, thus reducing power dissipation. However, the gradient field can include energy at a much lower frequency than the RF magnetic excitation field, which can more easily penetrate through the housing of the IMD. Unlike the field from the RF excitation pulse, the gradient field can more easily induce bulk eddy currents in one or more conductors within the IMD housing, such as within one or more circuits, capacitors, batteries, or other conductors.

Aside from heating, the EMF can create, among other things, non-physiologic voltages that can cause erroneous sensing of cardiac electrical activity, or the EMF can create a voltage sufficient to depolarize cardiac tissue or render the cardiac tissue refractory, possibly affecting pacing therapy. In an illustrative example, an IMD can be connected to one or more leads, such as one or more subcutaneous or intravascular leads positioned to monitor the patient, or to provide one or more therapies to the patient. In this illustrative example, a surface area of a "circuit" including the lead, the housing of the IMD, and a path through at least partially conductive body tissue between an electrode on the lead and the IMD housing can be more than 300 square centimeters, or more than 0.03 square meters. Thus, using Faraday's law, the EMF developed through the body tissue between the electrode (e.g., a distal tip or ring electrode) of the lead and the housing of the IMD can be more than 3 volts (e.g., more than 0.03 square meters times 100 t/s).

In an MR field, an item, such as an IMD, can be referred to as "MR Safe" if the item poses no known hazard in all MRI environments. In an example, MR Safe items can include non-conducting, non-metallic, non-magnetic items, such as a glass, porcelain, a non-conductive polymer, etc. An item can be referred to as "MR Conditional" in the MR field if the item has been demonstrated to pose no known hazards in a specified MRI environment with specified conditions of use (e.g., static magnetic field strength, spatial gradient, time-varying magnetic fields, RF fields, etc.). In certain examples, MR Conditional items can be labeled with testing results sufficient to characterize item behavior in a specified MRI environment. Testing can include, among other things, magnetically induced displacement or torque, heating, induced current or voltage, or one or more other factors. An item known to pose hazards in all MRI environments, such as a ferromagnetic scissors, can be referred to as "MR Unsafe."

Radiopacity refers to the relative inability of electromagnetism to pass through a particular material. Radiopaque materials can inhibit passage of electromagnetic radiation, such as X-Ray.

In an example, an IMD (e.g., a pacemaker, a defibrillator, or other cardiac rhythm management device), an implantable lead, or one or more other medical implants (e.g., stent, etc.) can include one or more radiopaque markers. The one or more radiopaque markers can be configured to allow tracking of the IMD, the implantable lead, or the other medical implant in the body, such as by using X-Ray, fluoroscopy, etc. In an example, the one or more radiopaque markers can include an identifier, viewable using electromagnetic radiation, the identifier configured to provide an indication that the IMD or the implantable lead bearing the identifier is MR Conditional. In an example, the identifier can include a wire wrapped around a portion of an implantable lead or a stamped radiopaque material located in a header or other dielectric housing of an IMD.

FIG. 1 illustrates generally an example of a system 100 including an IMD header 105 including a first lead port 110, a second lead port 111, a third lead port 112, and an identification (ID) cavity 115 configured to receive a first radiopaque X-Ray identifier 116. In this example, the first, second, and third lead ports 110, 111, 112 can be configured to receive respective first, second, and third leads (e.g., such as a right ventricular (RV) lead, a left ventricular (LV) lead, a right atrial (RA) lead, or one or more other leads). In an example, the first radiopaque X-Ray identifier 116 can include a stamped material configured to identify the manufacturer or model of the IMD, and, in certain examples, can be used to identify a compatible communication device or software for the IMD. In an example, the first radiopaque X-Ray identifier 116 can include an indication that the IMD is MR Conditional.

The present inventors have recognized, among other things, that it can be difficult to manufacture or provide a uniform sized and shaped identifier on an implantable lead using a wire wrapped around a portion of the implantable lead. Accordingly, the present inventors have recognized, among other things, that the identifier can include one or more radiopaque rings (e.g., platinum iridium rings, etc.) about one or more specified locations along the implantable lead (e.g., a rear seal, etc.). Further, the present inventors have recognized, among other things, that the identifier can include one or more identifiers having a specified configuration configured to provide specified information to a user, to a machine, or to an automated process using X-Ray, fluoroscopy, etc. (e.g., more information than simply the manufacturer, model, or whether the implantable lead is MR Conditional or not). In certain examples, a machine or an automated process can automatically recognize (e.g., using image processing, etc.) a specified configuration of the one or more identifiers.

Figure 2:
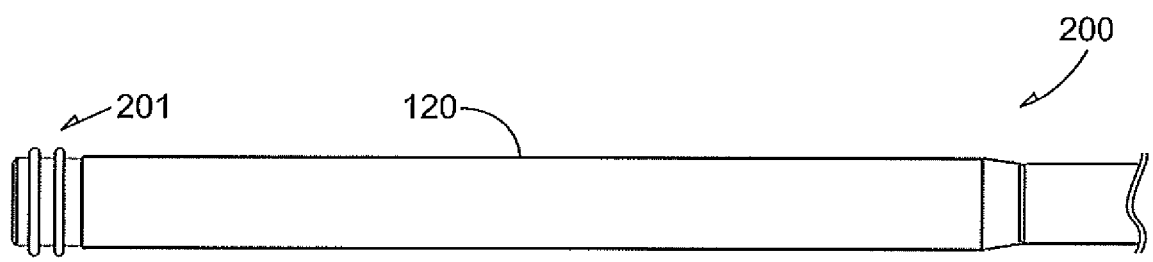
FIG. 2 illustrates generally an example of an implantable lead including a rear seal near a proximal end of the implantable lead.

FIG. 2 illustrates generally an example of an implantable lead 200 including a rear seal 120 near a proximal end 201 of the implantable lead 200. In an example, the proximal end 201 can be configured to be placed in a lead port (e.g., the first, second, or third lead ports 110, 111, 112) of an IMD header (e.g. the IMD header 105). The rear seal 120 can include a material thicker than the remainder of the implantable lead 200 (e.g., a thicker overmolded portion, such as to provide rigidity of the implantable lead 200 near the IMD header). In an example, the rear seal 120 can include a silicone or other material formed using an injection molding process.

Figure 3:
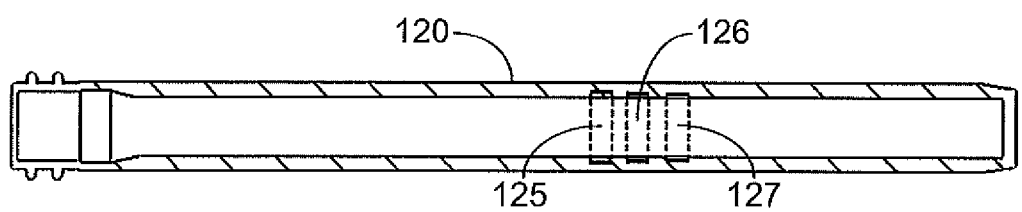
FIG. 3 illustrates generally an example of a cross section view of a rear seal of an implantable lead, the rear seal including a set of radiopaque identifiers.

FIG. 3 illustrates generally an example of a cross section view of a rear seal 120 of an implantable lead, the rear seal 120 including a set of radiopaque identifiers. In an example, the set of radiopaque identifiers can include a first radiopaque ring 125, a second radiopaque ring 126, and a third radiopaque ring 127. In other examples, the set of radiopaque identifiers can include more or less identifiers, the identifiers including radiopaque rings, other type identifiers, or combinations of different identifiers. In an example, the first, second, and third radiopaque rings 125, 126, 127 can include one or more different sized rings having a flat cross section, or one or more different cross section shapes. In the example of FIG. 3, the dashed lines of the first, second, and third radiopaque rings 125, 126, 127 illustrate the remainder of each ring circumventing the implantable lead 200. In other examples, the set of identifiers can include one or more equal, or substantially equal sized radiopaque rings having a flat cross section, or one or more other cross section shapes.

The present inventors have recognized, among other things, that placing the one or more identifiers about the rear seal 120 of an implantable lead (as opposed to placing the one or more identifiers about one or more other portions of the implantable lead 200) can provide a larger inner diameter of the set of identifiers (e.g., increasing the visibility or ease of identification of the identifiers using X-Ray, fluoroscopy, etc.). In other examples, identifiers different than (or in combination with) a radiopaque ring can be used, such as one or more identifiers having one or more different shapes than the example illustrated in FIG. 3 (e.g., rings having a round or partially curved cross section, such as to aid in visibility of the identifier, etc.).

The present inventors have recognized, among other things, that the number of identifiers, the shape or size of the identifiers, the spacing between the identifiers, or specific combinations of one or more of these or other characteristics of the identifiers can be used to provide a variety of information to a user, a machine, or an automated process. In an example, characteristics of the one or more identifiers (e.g., the number of identifiers, a pattern of different shaped or sized identifiers, etc.) can be used to indicate different levels of MR performance (e.g., that a device is MR Conditional in certain MRI environments). For example, the characteristics of the one or more identifiers can indicate that a device (e.g., an implantable lead, an IMD, etc.) is MR Conditional up to a certain the $B_0$ field (e.g., 1.5 Tesla, 3 Tesla, 7 Tesla, etc.), etc. In other examples, the characteristics of the one or more identifiers can indicate other information. For example, one or more characteristics or a set of characteristics of one or more identifiers on an implantable lead can indicate a lead type (e.g., a first number of identifiers can indicate that the implantable lead is a first type, such as a Bradycardia lead, a Tachycardia lead, a Heart Failure lead, etc., or an LV lead, an RV lead, an RA lead, etc., or one or more other lead types). In an example, the one or more characteristics can include physical characteristics (e.g., size, shape, number of identifiers, etc.), spatial characteristics (e.g., spacing, placement), or one or more other characteristics. In certain examples, the identifiers can include or be representative of a code (e.g., a binary or other code, a bar code, etc.) or other communication configured to provide information to a user, machine, or automated process.

Figure 4:
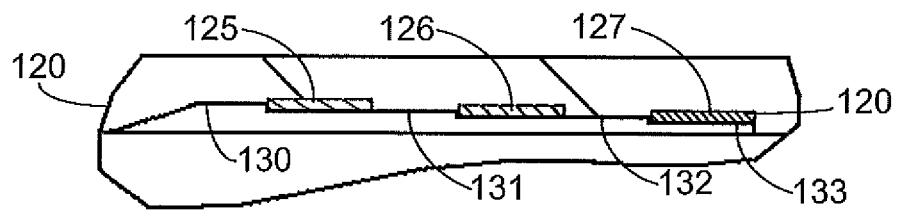
FIG. 4 illustrates generally an example of a cross section view of a portion of a rear seal of an implantable lead including a first radiopaque ring, a second radiopaque ring, and a third radiopaque ring.

FIG. 4 illustrates generally an example of a cross section view of a portion of a rear seal 120 of an implantable lead including a first radiopaque ring 125, a second radiopaque ring 126, and a third radiopaque ring 127.

In an example, the one or more identifiers (e.g., the first, second, and third radiopaque rings 125, 126, 127, etc.) can be imbedded into the rear seal 120 of the implantable lead 200 using a single shot mold injection process. In an example, during the injection molding process, the one or more identifiers can be inserted over a core pin having varying cross sections configured to position and retain the one or more identifiers having different inner diameters during the injection molding process.

The example of FIG. 4 illustrates a unique rear seal cross section including a first section 130, a second cross section 131, a third cross section 132, and a fourth cross section 133. In certain examples, the unique cross section can include one or more sections configured to provide passage in the axial direction to allow silicone or other material to flow around the inner diameters of the one or more identifiers. In an example, the unique rear seal cross sections can allow the one or more identifiers to be positioned and secured radially and axially on the core pin during the injection molding process.

In an example, the first radiopaque ring 125 can include an inner diameter of 0.096 inches, a width of 0.030 inches, and a thickness of 0.0030 inches. The second radiopaque ring 126 can include an inner diameter of 0.093 inches, a width of 0.030 inches, and a thickness of 0.0030 inches. The third radiopaque ring 127 can include a diameter of 0.090 inches, a width of 0.030 inches, and a thickness of 0.0030 inches. And further, the spacing between the first, second, and third markers 125, 126, 127 can include 0.025 inches. In this example, the first, second, and third radiopaque rings 125, 126, 127 can be used, in combination with the stepped cross sections illustrated in FIG. 4 having corresponding measurements, to provide a simple manufacturing process where each ring can be easily positioned in an intended position.

In other examples, one or more of the first, second, or third radiopaque rings 125, 126, 127 or the first, second, third, or fourth cross sections 130, 131, 132, 133 can include one or more other diameters, widths, or thicknesses than those listed above, or generally, different identifiers can include different sizes, shapes, etc. Further, more or less identifiers (e.g., more than three or less than three) or corresponding cross sections can be used, and in certain examples, the spacing between the radiopaque rings can be different than that listed above or can vary between identifiers.

Figure 5:
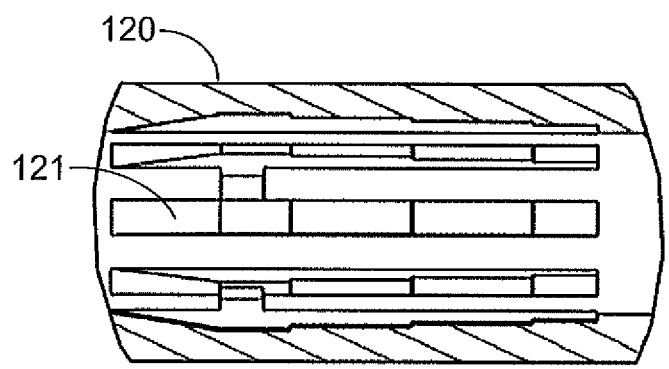
FIG. 5 illustrates generally an example of an axial view of a portion of a rear seal of an implantable lead including a plurality of separate alignment regions (e.g., a first alignment region) configured to align or imbed one or more identifiers.

FIG. 5 illustrates generally an example of an axial view of a portion of a rear seal 120 of an implantable lead including a plurality of separate alignment regions (e.g., a first alignment region 121) configured to align or imbed one or more identifiers. In an example, each alignment region can include the one or more unique cross sections of the example of FIG. 4. In other examples, one or more other cross sections can be used depending on the characteristics of the one or more identifiers.

Figure 6:
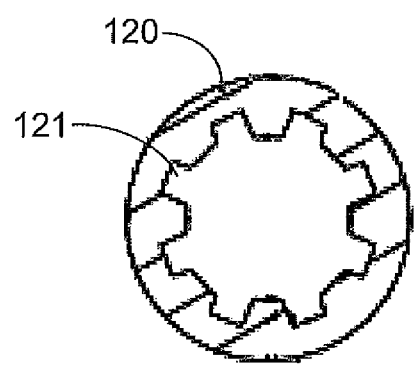
FIG. 6 illustrates generally an example of a radial view of a portion of a rear seal of an implantable lead including a plurality of separate alignment regions (e.g., a first alignment region) configured to align or imbed one or more identifiers.

FIG. 6 illustrates generally an example of a radial view of a portion of a rear seal 120 of an implantable lead including a plurality of separate alignment regions (e.g., a first alignment region 121) configured to align or imbed one or more identifiers. In an example, a core pin can be used in the manufacturing process including one or more fins or raised stepped sections configured to hold each identifier in an intended position and allow a material to flow between the core pin and an outer mold, at least partially surrounding each identifier. In other examples, one or more other shapes (e.g., having more or less raised sections, etc.) can be used.

Figure 7:
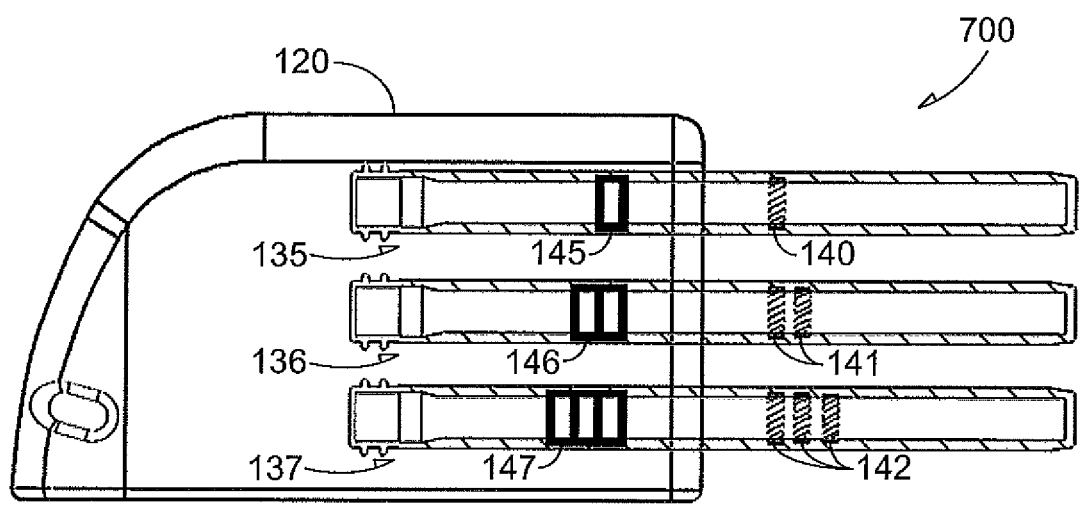
FIG. 7 illustrates generally an example of a system including an IMD header, a first implantable lead including a first identifier (e.g., a first radiopaque ring, etc.), a second implantable lead including a second identifier, and a third implantable lead including a third identifier.

FIG. 7 illustrates generally an example of a system 700 including an IMD header 120, a first implantable lead 135 including a first identifier 140 (e.g., a first radiopaque ring, etc.), a second implantable lead 136 including a second identifier 141, and a third implantable lead 137 including a third identifier 142. In an example, the IMD header 120 can include a third identifier 145, a fourth identifier 146, and a fifth identifier 147 (e.g., a radiopaque identifier, etc.). In an example, one or more of the third, fourth, or fifth identifiers 145, 146, 147 can include a stamped or other material configured to be visible using X-Ray, fluoroscopy, etc. (e.g., the first radiopaque X-Ray identifier 116), and in certain examples, can be included in an ID cavity (e.g., the ID cavity 115) located proximate an associated implantable lead. In other examples, one or more different identifiers, numbers of identifiers, etc. can be used.

In an example, the IMD header 120 can include one or more identifiers (e.g., the third, fourth, and fifth identifiers 145, 146, 147, etc.) configured to match one or more identifiers of one or more implantable leads (e.g., the first identifier 140 of the first implantable lead 135, the second identifier 141 of the second implantable lead 136, and the third identifier 142 of the third implantable lead 137). In an example, using radiopaque imaging, the one or more identifiers of the IMD header 120 or one or more of the implantable leads can be used to identify a specific lead port of the IMD header 120, to match a specific implantable lead to a specific lead port (e.g., to test or ensure that the correct implantable lead was placed in the correct lead port), or to provide other information about the IMD header 120, the IMD, the implantable lead, etc.

In other examples, one or more identifiers (e.g., identifiers of the IMD header 120 or identifiers of the one or more implantable leads) can be used to test or ensure that the implantable lead was inserted into the lead port of the IMD to a correct depth, or to test for proper lead connection (e.g., due to incorrect attachment, or due to lead migration over a period of time). In an example, an identifier on a lead can be configured to line up with, fill, overlap, etc. one or more radiopaque feature (or absence of a radiopaque feature) of the IMD header 120 when fully inserted into the lead port. In an example, using X-Ray, fluoroscopy, etc., if the implantable lead becomes detached or partially removed, the alignment, fill, overlap, etc. can change, indicating said movement. Further, in certain examples, the one or more identifiers can be used to detect axial movement between the IMD header 120 and an implantable lead over time. In other examples, the one or more identifiers can be used to communicate other information.

Figure 8:
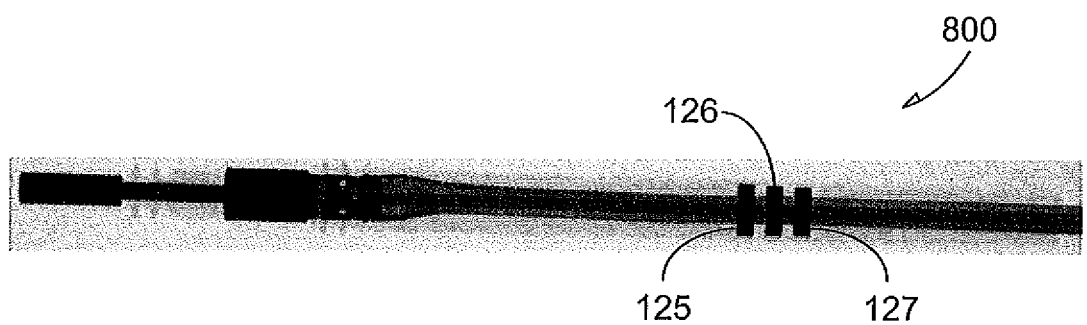
FIG. 8 illustrates generally an example of a radiopaque image (e.g., an X-Ray image) of an implantable lead including a first radiopaque ring, a second radiopaque ring, and a third radiopaque ring.

FIG. 8 illustrates generally an example of a radiopaque image (e.g., an X-Ray image) of an implantable lead 800 including a first radiopaque ring 125, a second radiopaque ring 126, and a third radiopaque ring 127.

In other examples, other technologies different than injection molding can be used to imbed or otherwise place the one or more identifiers, including swaging, adhesives, pastes that have radiopaque particles, etc.

In an example, a system can include a plurality of radiopaque rings about at least a portion of an implantable lead (e.g., a rear seal) separated by non-radiopaque material (e.g., non-radiopaque rings). In certain examples, the radiopaque rings or the non-radiopaque material can include various shapes, widths, inner or outer diameters, thicknesses, spacing, etc.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. A system comprising:
    an implantable lead including:
        a plurality of radiopaque rings arranged in a specified configuration about a portion of the implantable lead; and
    wherein the specified configuration of the plurality of radiopaque rings is configured to provide specified information to a user, to a machine, or to an automated process; and
    wherein the specified configuration is selected from a first specified configuration of the plurality of radiopaque rings that is configured to provide an indication that the implantable lead is MR compatible to a first magnetic field strength, and a second specified configuration that is configured to provide an indication that the implantable lead is MR compatible to a second magnetic field strength, the second specified configuration different than the first specified configuration and the second magnetic field strength different than the first magnetic field strength.

2. The system of claim 1, wherein each of the plurality of radiopaque rings have different inner diameters.

3. The system of claim 1, wherein the implantable lead includes a rear seal configured to be at least partially inserted into a lead port of an implantable medical device (IMD) header; and
    wherein the plurality of radiopaque rings are configured to be injection molded into the rear seal.

4. The system of claim 1, wherein the specified configuration of the plurality of radiopaque rings includes the number of radiopaque rings, and wherein different numbers of radiopaque rings are configured to provide different information about the MR compatibility of the implantable lead.

5. The system of claim 1, wherein the specified configuration of the plurality of radiopaque rings includes a radiopaque ring shape.

6. The system of claim 5, wherein different radiopaque ring shapes are configured to provide different information about the implantable lead itself or about an implantable medical device coupled to the implantable lead.

7. The system of claim 1, wherein the first specified configuration includes a first number of radiopaque rings and the second specified configuration includes a second number of radiopaque rings, the second number different than the first number.

8. A system comprising:
    an implantable lead including:
        a rear seal configured to be at least inserted into a lead port of an implantable medical device (IMD) header; and
        a plurality of radiopaque rings each having different inner diameters arranged in a specified configuration about a portion of the implantable lead, wherein the plurality of radiopaque rings are configured to be injection molded into the rear seal; and wherein the specified configuration of the plurality of radiopaque rings provides an indication of a level of magnetic resonance (MR) compatibility of the implantable lead;

wherein a first specified configuration is configured to provide an indication that the implantable lead is MR Conditional to a first magnetic field strength and a second specified configuration is configured to provide an indication the implantable lead is MR Conditional to a second magnetic field strength, the second specified configuration different than the first specified configuration and the second magnetic field strength different than the first magnetic field strength; and wherein the first specified configuration includes a first number of radiopaque rings and the second specified configuration includes a second number of radiopaque rings, the second number different than the first number.

9. The system of claim 1, comprising a machine configured to receive and automatically recognize the specified configuration.

10. The system of claim 8, comprising a machine configured to receive and automatically recognize the specified configuration.

11. The system of claim 1, wherein the specified configuration of the plurality of radiopaque rings includes at least one of a radiopaque ring inner or outer diameter, and wherein different inner or outer diameters are configured to provide different information about the implantable lead itself or about an implantable medical device coupled to the implantable lead.

12. The system of claim 1, wherein the specified configuration of the plurality of radiopaque rings includes one or more spacings between radiopaque rings, and wherein different spacings between radiopaque rings are configured to provide different information about the implantable lead itself or about an implantable medical device coupled to the implantable lead.

13. The system of claim 1, wherein the specified configuration of the plurality of radiopaque rings includes a combination of at least two or more of a radiopaque ring shape, a radiopaque ring inner or outer diameter, or one or more spacings between radiopaque rings, and wherein different combinations are configured to provide different information about the implantable lead itself or about an implantable medical device coupled to the implantable lead.

14. The system of claim 1, wherein at least one of the radiopaque rings comprises a platinum-iridium alloy.

15. The system of claim 8, wherein at least one of the radiopaque rings comprises a platinum-iridium alloy.

16. The system of claim 1, comprising a rear seal configured to at least partially surround at least one of the radiopaque rings.

17. A system comprising:

an implantable medical device; and an implantable lead, configured to be coupled to the implantable medical device, including:

a rear seal configured to be at least partially inserted into a lead port of a header of the implantable medical device; and a plurality of radiopaque rings, each ring having a ring characteristic, wherein the plurality of radiopaque rings are configured to be injection molded into the rear seal in a specified configuration about a portion of the implantable lead;

wherein a first specified configuration of the plurality of radiopaque rings indicates that the implantable lead is MR compatible to a first magnetic field strength;

wherein a second specified configuration of the plurality of radiopaque rings indicates that the implantable lead is MR compatible to a different second magnetic field strength; and wherein each ring of the plurality of radiopaque rings includes at least one different ring characteristic selected from the group consisting of a radiopaque ring shape, a radiopaque ring inner or outer diameter, and a spacing from an adjacent radiopaque ring.

* * * * *